US006666065B2

(12) United States Patent
Gilson et al.

(10) Patent No.: US 6,666,065 B2
(45) Date of Patent: Dec. 23, 2003

(54) PROBE TIP ALIGNMENT FOR PRECISION LIQUID HANDLER

(75) Inventors: Robert E. Gilson, Middleton, WI (US); Robert Norton, Madison, WI (US)

(73) Assignee: Gilson, Inc., Middleton, WI (US)

( * ) Notice: Subject to any disclaimer, the term of this patent is extended or adjusted under 35 U.S.C. 154(b) by 0 days.

(21) Appl. No.: 10/202,040

(22) Filed: Jul. 24, 2002

(65) Prior Publication Data

US 2002/0178779 A1 Dec. 5, 2002

Related U.S. Application Data

(62) Division of application No. 09/769,569, filed on Jan. 24, 2001, now Pat. No. 6,474,181.

(51) Int. Cl.[7] .................................................. G01N 1/00
(52) U.S. Cl. ...................................................... 73/1.01
(58) Field of Search ............................... 73/1.01, 866.5, 73/864.25, 863.32, 864.17, 1.74, 1.79, 1.81; 29/407.01, 407.05, 407.08, 402.19, 592

(56) References Cited

U.S. PATENT DOCUMENTS 5,270,210 A   12/1993   Weyrauch et al.

*Primary Examiner*—Robert Raevis
(74) *Attorney, Agent, or Firm*—Greer, Burns & Crain, Ltd.; Philip M. Kolehmainen

(57) ABSTRACT

A probe drive system of a precision liquid handler sequentially inserts probe tips of a multiple probe array into a locator well at a known position on a locator bed. The position of each probe tip is determined by driving the probe tip into contact with points on the side wall of the locator well and sensing the contracts. The positions of the probe tips are mapped and checked for skew of the probe array. The probe tip positions are overlaid to determine probe tip scatter. If a probe tip is excessively misaligned, it is inserted into the locator well and driven against the side wall to bend the probe and reduce the misalignment of the probe tip. The center of the probe tip scatter is determined and is used by the probe drive system as a global correction factor. Probe tips with known positions are inserted into spaced apart locator wells to detect skew of the locator bed.

8 Claims, 5 Drawing Sheets

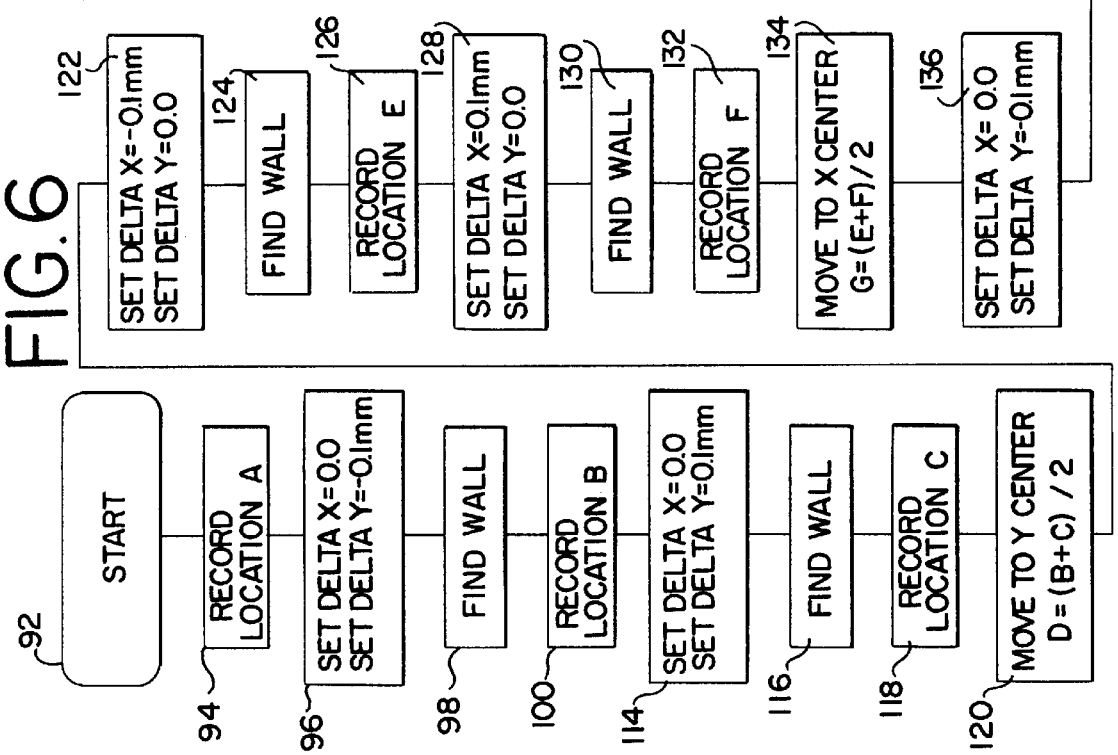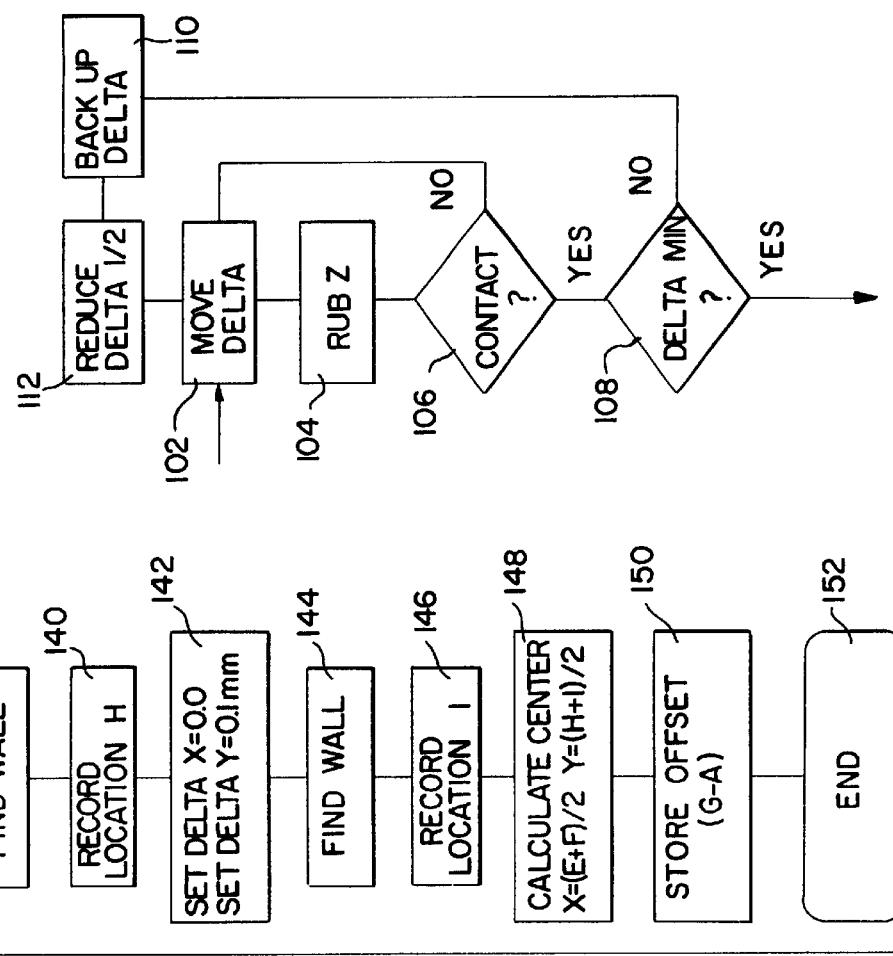

PROBE TIP ALIGNMENT FOR PRECISION LIQUID HANDLER

This is a divisional U.S. application of application Ser. No. 09/769,569 filed on Jan. 24, 2001, now U.S. Pat. No. 6,474,181.

FIELD OF THE INVENTION

The present invention relates to aligning the probe tips of a precision automated liquid handler.

DESCRIPTION OF THE PRIOR ART

In pharmaceutical, genomic and proteomic research and drug development laboratories, and other biotechnology applications, automated liquid handlers are used for handling laboratory samples in a variety of laboratory procedures. For example, liquid handlers are used for biotechnological and pharmaceutical liquid assay procedures, sample preparation, compound distribution, microarray manufacturing and the like. An automated liquid handler has a work bed that supports an array of sample receptacles. One-piece sample containing plates having an integral array of many sample containing receptacles or wells are widely used. The liquid handler has an array of multiple probes that are moved into alignment with one or more sample containing wells to carry out liquid handling operations such as adding liquid to the wells.

It is desirable to decrease the volumes of samples treated with automated liquid handlers. Sample containing plates with a footprint of about three and one-half by five inches and having an X-Y array of 96 wells in an eight by twelve well pattern have been widely used. In order to increase throughput and to reduce consumption of sample constituents, these plates are being superceded by microplates of the same footprint but having an array of smaller wells, for example 384 wells in a sixteen by twenty-four array. This trend is continuing, and there is a need for an automated liquid handler able to accommodate microtiter plates having a very dense array of a very large number of very small volume wells with volumes in the nanoliter range. High density microplates presently in use, with the same footprint as previously used plates, have 1,536 wells in a thirty-two by forty-eight well array.

Microtiter plates with a dense array of small, closely spaced wells present serious problems for an automated liquid handler. In operation, the handler must be precise enough to place every probe of a multiple probe array into alignment with a corresponding number of sample containing wells. As well size and spacing decreases, it becomes more difficult for an automated handler to reliably place the liquid handling probes directly over selected sample containing wells.

The margin for error in positioning the probes relative to the plates and wells decreases as well array density increases. One aspect of the problem is the precise location and alignment of the probe tips. If the group of probes is misaligned, or if individual probes of the group are out of position relative to other probes of the group, then it may not be possible to locate each probe of the group directly over a sample well of the plate. It is time consuming and difficult manually to check and reposition the probes to be sure they are properly positioned and aligned. Even if the probes are initially set up correctly, they can become displaced from their intended positions after a period of use. It would be desirable to provide an automated system for quickly and accurately checking and correcting probe tip positioning and alignment without substantial operator time and skill.

SUMMARY OF THE INVENTION

A principal object of the present invention is to provide an improved method for aligning probe tips of a precision liquid handler. Other objects are to provide a probe tip locating method using an electrical sensing capability that may preexist in the liquid handler; to provide a probe tip alignment method for detecting skew of a multiple probe array; to provide a probe tip alignment method for detecting misaligned probes and for bending a misaligned probe into an aligned position; to provide a probe tip alignment method that detects locator bed skew; to provide a probe tip alignment method that determines a center of probe scatter for use as a correction factor for a probe drive system; and to provide a probe tip alignment method that is automated and does not require operator time and skill.

In brief, in accordance with the invention, there is provided a probe tip alignment method for a precision liquid handler having a probe array moved by a probe drive system relative to a locator bed holding sample wells. The method includes sequentially inserting the probe tips of the probe array with the probe drive system into a locator well at a known position on the locator bed, then sequentially sensing the position of each probe tip in the locator well, and then mapping the positions of the probe tips.

BRIEF DESCRIPTION OF THE DRAWING

The present invention together with the above and other objects and advantages may best be understood from the following detailed description of the preferred embodiment of the invention illustrated in the drawings, wherein:

FIG. 6 is a flow chart of steps in carrying out the routine shown diagrammatically in FIG. 5;

FIG. 7 is a flow chart of a wall finding subroutine used in the routine of FIG. 6;

DETAILED DESCRIPTION OF THE PREFERRED EMBODIMENT

Figure 1:
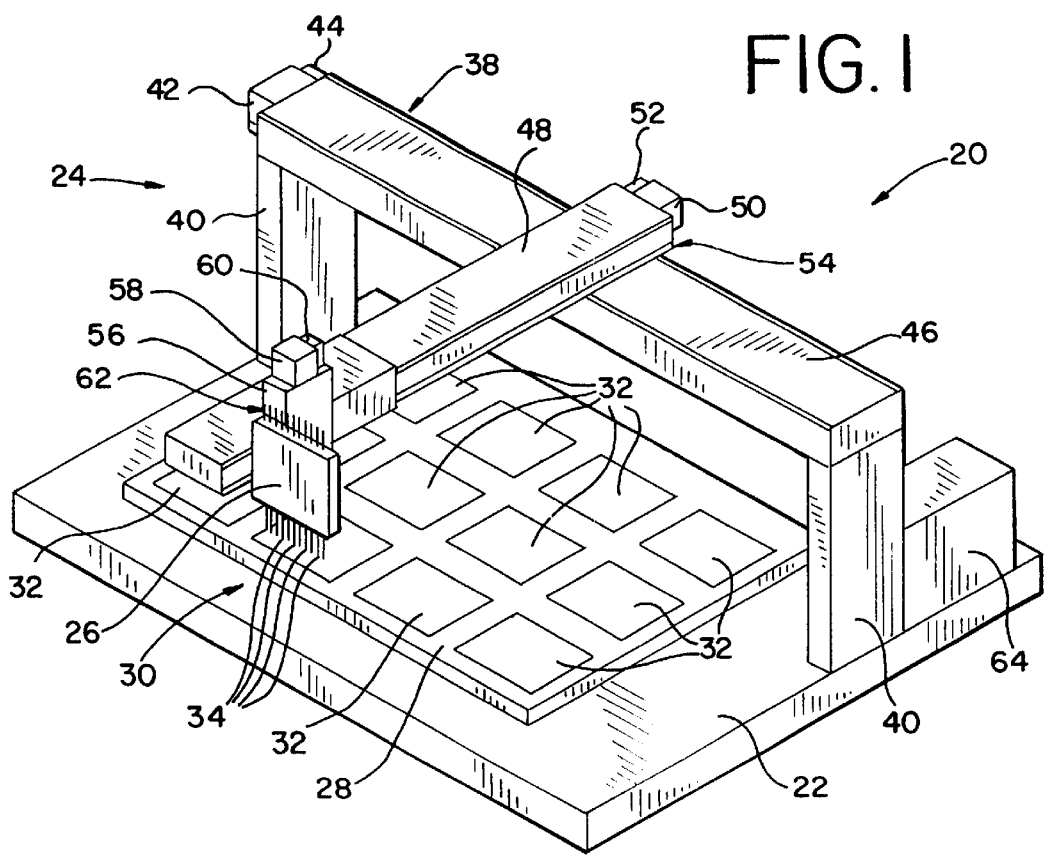
FIG. 1 is a simplified, diagrammatic, isometric view of a representative precision automated liquid handler with which the method of the present invention can be performed.

Having reference now to the drawings, and initially to FIG. 1, there is shown in simplified, diagrammatic form an example of an automated precision liquid handler generally designated as 20. The liquid handler 20 includes a table or work bed 22 below an X-Y-Z probe drive system 24 carrying a probe holder 26. A locator bed 28 is supported on the surface of the work bed 22. The locator bed 28 supports a number of high density sample containing microplates 32. The probe holder 26 supports a multiple probe array 30 of individual probes 34 each having a probe tip 36. In the preferred embodiment of the invention, the array 30 includes twelve probes 34 in a common plane, although other arrays and different numbers of probes could be used. The preset invention is concerned with aligning the probe tips 36 in predetermined positions along a straight line oriented relative to the locator bed so that the probe tips are moved by the drive system 24 into accurate registration with the high density microplates 32.

The X-Y-Z probe drive system 24 moves the probe holder 26 above the work bed 22 and positions it with great precision in predetermined positions relative to the work bed 22. The system 24 includes an X drive assembly 38 mounted above and to the rear of the work bed 22 by suitable supports 40. An X drive motor 42, with an encoder 44, operates a mechanism within an X arm 46 to move a Y arm 48 from side to side in the X direction. A Y drive motor 50, with an encoder 52, of a Y drive assembly 54 operates a mechanism within the Y arm 48 to move a Z arm 56 forward and back in the Y direction. A Z drive motor 58, with an encoder 60, of a Z drive assembly 62 operates a mechanism within the Z arm 56 to move the probe holder 26 up and down in the Z direction. Linear encoders may be used in place of the illustrated encoders 44, 52 and 60.

The liquid handler 20 includes a programmable controller 64 connected to the motors 42, 50 and 58 and to the encoders 44, 52 and 60 or other encoders. Controller 64 includes a microprocessor and an operating system capable of controlling the motion of the probe holder 26 in accordance with programmed instructions saved in memory of the controller and/or communicated to the controller from a remote source. Controller 64 using position feedback signals from the X, Y and Z encoders is able to position the probe holder 26 accurately precisely, within a very small margin of error in the microns range.

Each micro plate 32 includes an array of many individual sample containing wells 66. The plate 32 has a footprint of about three and one-half by five inches, and known plates may have an X-Y array of 96 wells in an eight by twelve well pattern, or an array of 384 smaller wells in a sixteen by twenty-four array, or a high density array of 1,536 nanoliter volume wells in a thirty-two by forty-eight well pattern. The method of the present invention is particularly advantageous when the liquid handler is used to dispense nanoliter volumes into small sample wells of high density microplates and arrays.

Figure 2:
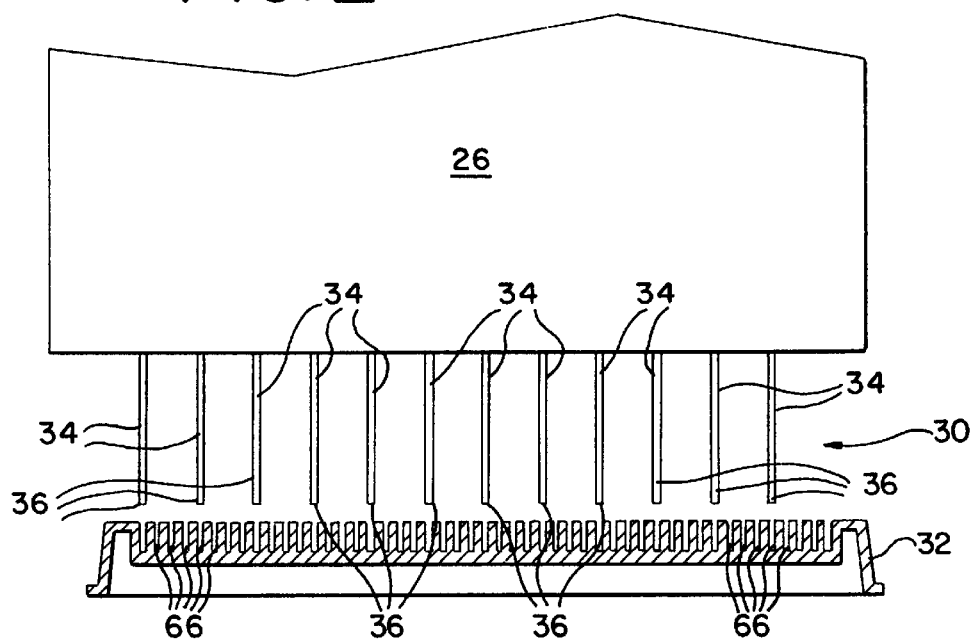
FIG. 2 is an enlarged, fragmentary front view of the probe carrier and multiple probe array of the precision liquid handler of FIG. 1, showing the probes in registration with wells of a high density microplate.

A cross sectional view of a high density microplate 32 of is seen in FIG. 2, along with the probe holder 26 carrying twelve individual probes 34. The microplate 32 includes thirty-two rows extending in the X direction, each having forty-eight sample wells 66. One row 64 is seen in FIG. 2. Each well 66 has a length and a width of 1.2 millimeters and the center to center well spacing is 2.25 millimeters. The probes 34 are on 9 millimeter centers (spanning five wells 66) and the diameter of each probe tip 36 is 1.1 millimeters.

Each probe tip 36 can discharge liquid in a droplet size of 0.2 millimeter. The probe holder 26 is moved to the location seen in FIG. 2 to distribute liquid to the twelve wells 66 that are aligned under the probe tips 36. The probe holder 26 is then moved by the X-Y-Z probe drive system 24 to align the probe tips 36 with another set of wells 66. In this manner some or all of the wells 66 of the plate 32, and of some or all of the plates 32, can be supplied with nanoliter volumes of liquid. Because of the small well size and spacing, and the small probe size and spacing, great precision is required. In order to assure that ejected droplets are dispensed into the intended sample wells 66, and to assure that the droplets fall cleanly into the sample wells 66, the probe tips 36 must be precisely aligned, and accurate probe tip position information must be available for use by the controller 64.

Figure 3:
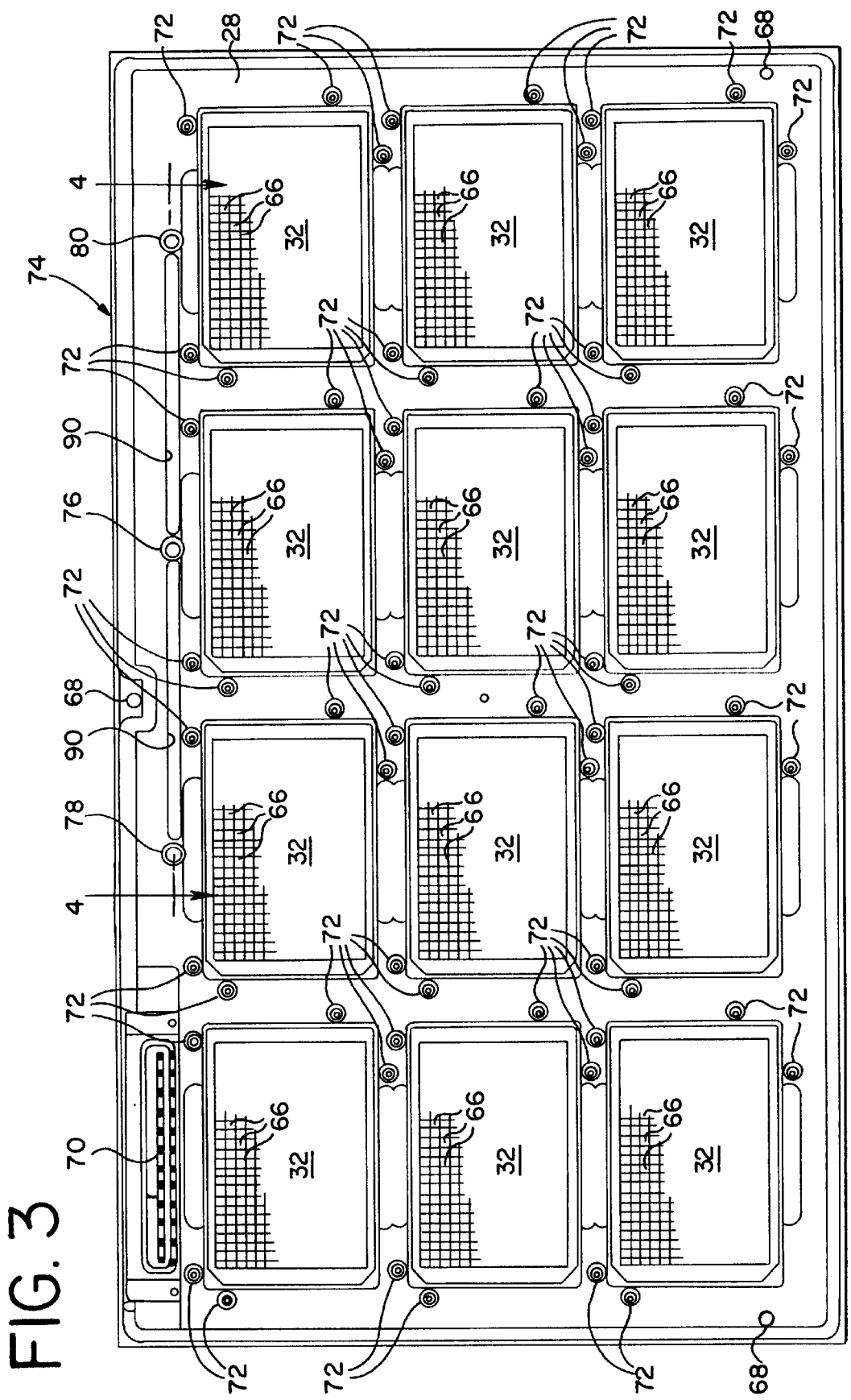
FIG. 3 is a top plan view of the locator bed of the precision automated liquid handler of FIG. 1.

FIG. 3 shows the locator bed 28, preferably a thick, stable plate of metal such as aluminum supported upon the work bed of 32 the liquid handler 20. Three leveling and locating points 68 permit the location and orientation of the locator bed 28 to be precisely adjusted and fixed on the work bed 22. The locator bed 28 includes a probe rinse station 70 and a system of posts 72 for positioning and holding an array of twelve microplates 32 in precisely determined positions upon the locator bed 28. The plates 32 have a consistent, known configuration, and are held by the posts 72 in precisely fixed positions on the locator bed 28. Therefore, if the locator plate is correctly positioned, without skew, on the work bed 22, and if the probe tips 36 a are properly aligned and positioned, the probe drive system 24 can position the probe tips 36 in precise registration with a selected group of sample wells 66.

Figure 4:
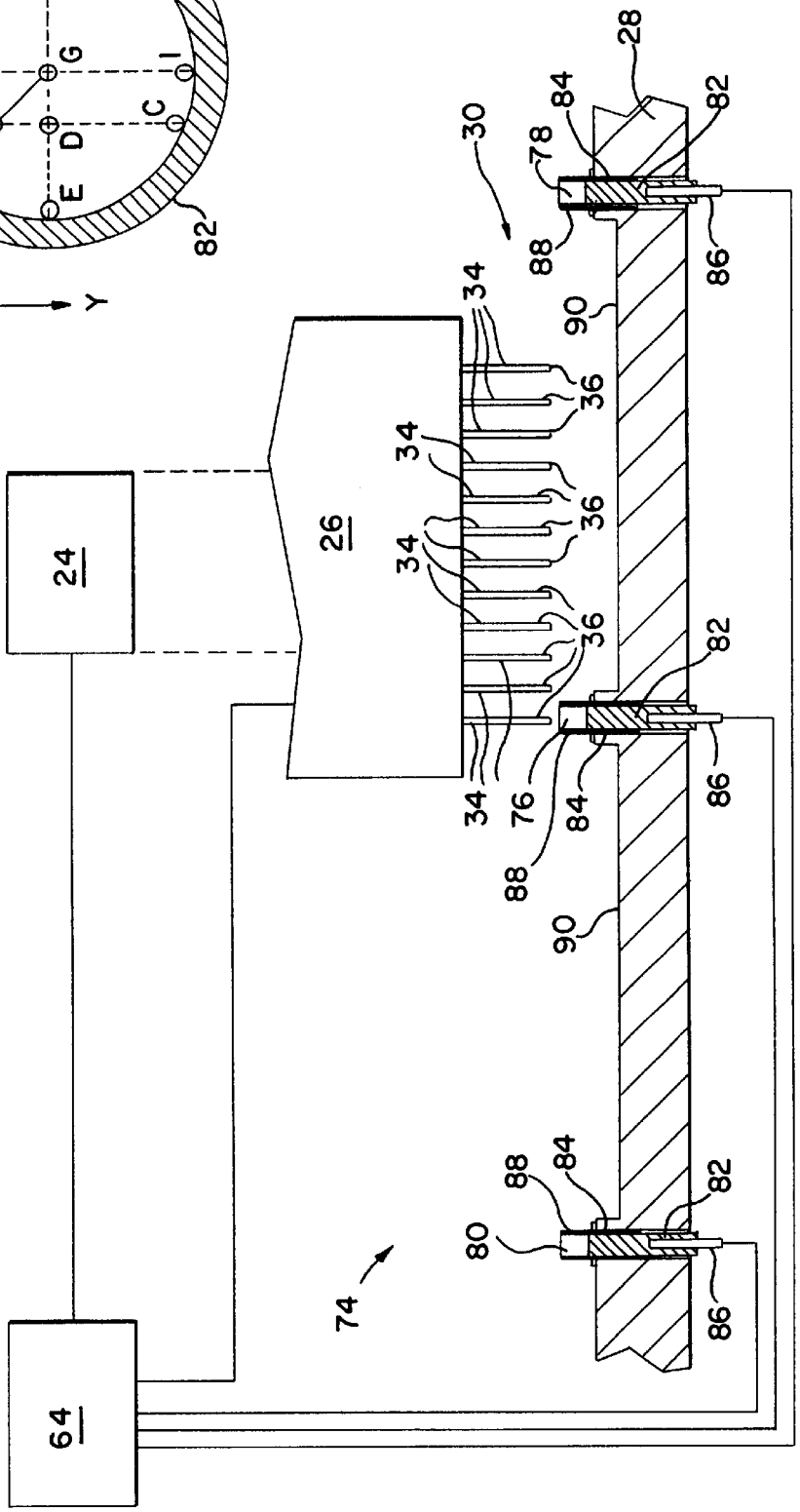
FIG. 4 is a fragmentary, enlarged, cross sectional view of the locator bed of FIG. 3, taken along the line 4—4 of FIG. 3, together with a schematic block diagram of other components of the precision automated liquid handler of FIG. 1.

In accordance with the invention, the locator bed 28 includes a probe locator station generally designated as 74. The locator station 74 includes three probe tip locator wells 76, 78 and 80 aligned in a straight line in the X direction along the rear portion of the locator bed 28. The locator wells 76, 78 and 80 are preferably equidistant from one another and are spaced apart by a distance greater than the length of the probe array 30 (FIG. 4). Each locator well 76, 78 and 30 includes a metal, electrically conductive post 82 carried by an insulating bushing 84 received in a hole extending vertically through the locator bed 28. An electrical terminal 86 is connected to the bottom of each post 82 beneath the locator bed 28. A well 76, 78 or 80 is formed as an axially aligned opening in the top of each post 82. Each well has a diameter of about 8 millimeters and a depth of about 6 millimeters and is surrounded by a continuous, circular cylindrical side wall 88 with a thickness of about one millimeter. Recessed clearance areas 90 are provided between the wells 76 and 78 and between the wells 76 and 80.

In performing the probe tip alignment method of the present invention, the probe tips 36 are sequentially inserted into the locator well 76 by the drive system 24 and probe holder 26. The area of the target provided by the well 76 is far larger than a probe tip 36 and is large enough to receive a probe tip 36 even if it is misaligned, for example by bending of the corresponding probe 34 or variations in the mounting of the corresponding probe 34. After each probe tip 36 is inserted into the locator well 76, the position of the probe tip 36 is detected and its offset from an ideal or nominal aligned position in the array 30 is recorded. When the position and offset information is obtained for each of the probe tips 36 of the probe array 30, this information is used, if necessary, to correct the position of any seriously misaligned probe tip 36, to correct skew of the probe array 30 and to permit the controller 64 to correct for probe tip cluster offset in operating the drive system 24.

Figure 5:
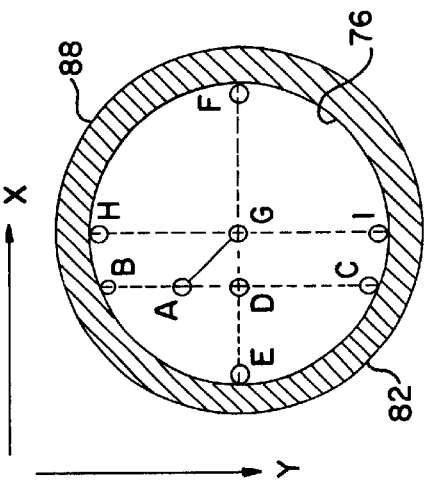
FIG. 5 is an enlarged sectional view of a locator well, including a diagrammatic illustration of a routine for finding the offset of a probe tip from a nominal or ideal aligned position in a probe array.

A routine for detecting probe tip position and offset is illustrated in FIGS. 5–7. This routine is carried out in accordance with programmed instructions implemented by the controller 64. As seen in FIG. 5, in order to insert a probe tip 36 into the locator well 76, the controller 64 operates the drive system 24 to place the probe tip 36 at a position that would be at the center of the well 76 if the probe tip 36 were precisely aligned at its nominal position in the probe array 30. However, the probe tip 36 normally is offset at some distance from the ideal position. As seen in the example of FIG. 5, the probe tip 36 is initially located at the position designated as A. The routine of FIG. 6 is then performed to measure the probe position and offset.

The probe measuring routine commences at start block 92 and at block 94 this initial position A is recorded for subsequent calculation in the course of the routine. Then, as indicated at blocks 96 and 98, the probe tip 36 is moved in the negative Y direction (upward as seen in FIG. 5) until the probe tip contacts the side wall 88 of the locator well 76. This contact is sensed electrically. More specifically, the controller 64 is connected to both the conductive probe holder 26 and each conductive probe 34, and is also connected to the electrical terminal 86 of the locator well 76. A small dc voltage, for example four volts, is applied to the locator well 76 and the probes 34 are at ground potential. When the probe tip 36 contacts the wall 88, the resulting electrical signal is used by the controller 64 to detect the contact. An advantage of this sensing approach is that the liquid handler 20 may include preexisting electrical sensing capability for use in liquid level detection in applications where the probes 34 can descend into larger wells of less dense plates. The point of contact resulting from movement in the negative Y direction is designated as B in FIG. 5. In block 100 this location is stored for further use.

The preferred subroutine called in block 98 for finding the wall 88 is illustrated in detail in FIG. 7. Before the find wall subroutine is called, an increment of probe tip movement, delta, is set in block 96. For movement in the negative Y direction, delta is set to negative 0.1 mm in the Y direction. The subroutine of FIG. 7 commences at block 102 where the probe tip 36 is moved 0.1 mm in the negative Y direction. At the end of this motion, at block 104, the probe tip is moved up and down in the Z direction. The purpose of this motion is to establish a good electrical contact between the probe tip 36 and the wall 88 if the probe tip 36 has reached the wall 88. The presence or absence of this contact is tested in decision block 106. If there is no contact, the subroutine returns to block 104, and continues to loop, moving the probe tip 36 in increments of delta until contact is sensed between the probe tip 36 and the wall 88 at point B.

This portion of the FIG. 7 subroutine locates point B with an accuracy limited by the size of the initial delta, 0.1 mm. Any overtravel of the probe tip 36 after initial contact against the wall 88 at the maximum delta value is well within the elastic limit of the probe 34 and does not cause permanent deformation. To increase the measuring resolution and achieve a more accurate measurement, at block 108 and block 110 the probe tip 36 is moved in the reverse direction, back away from the wall 88. Then at block 112, delta is halved, and the subroutine returns to block 102 described above. When contact again occurs, at block 108 the present value of delta is compared with a minimum increment to providing the desired accuracy. For example, the minimum delta value may be in the order of microns, consistent with the positional accuracy of the probe drive system 24. If delta is larger than the stored minimum, the subroutine returns again to blocks 110, 112 and 102 and the value of delta is again decreased. This loop continues until contact is sensed at a resolution determined by the minimum delta value. At this point the routine returns to block 100 of FIG. 6 where the resulting value of position B is stored.

The next step is to move the probe tip 36 in the positive Y direction (down as seen in FIG. 5) to find another point of contact with wall 88 aligned in the Y direction. This point is designated as C in FIG. 5. In block 114 of FIG. 6, delta is set to 0.1 mm in the positive Y direction and the find wall subroutine of FIG. 7 is called in block 116. The position of location C is returned and stored at block 118.

The center of a line between points B and C is roughly on a Y diameter of the circular wall 88. In block 120 this point, designated as D in FIG. 5, is calculated by averaging the values of positions B and C, and the probe tip 36 is moved to this point D. Then the probe tip 36 is moved in the transverse X direction to find opposed points of contact E and F along the X axis. Delta is set to the negative X direction in block 122 and the find wall subroutine is called in block 124. The location of point E is returned and stored at block 126. Similarly, delta is set to the positive X direction in block 128 and the find wall subroutine is called in block 130. The location of point F is returned and stored at block 132.

The center of a line between points E and F is on an X diameter of the circular wall 88. In block 134 this point, designated as G in FIG. 5, is calculated by averaging the values of positions E and F, and the probe tip 36 is moved to this point G. Because the point D can be determined by non perpendicular contact of the probe tip 36 with the wall 88, and because the line B-C may be substantially offset from the X diameter of the wall 88, the probe tip 36 is moved again in the Y direction to find opposed points of contact H and I along the Y diameter to obtain an accurate measurement in the Y direction. Delta is set to the negative Y direction in block 136 and the find wall subroutine is called in block 138. The location of point H is returned and stored at block 140. Similarly, delta is set to the positive Y direction in block 142 and the find wall subroutine is called in block 144. The location of point I is returned and stored at block 146.

The Y coordinate of the center point G is recalculated in block 148 by averaging points H and I in the Y direction. The offset of the probe tip 36 at point A in FIG. 5 from the center point G is indicated by the line A-G. This offset is calculated at block 150 by subtracting the coordinates of point A from the coordinates of point G, and the offset is stored for subsequent use in the probe tip alignment method. The routine terminates at stop block 152.

Figure 8:
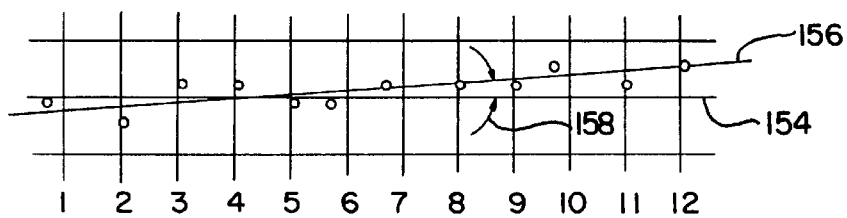
FIG. 8 is a diagram showing the measured probe tip offsets used for detecting probe holder skew.

The probe position and offset routine of FIGS. 5–7 is repeated for each of the twelve probe tips 36 in sequence until offset coordinates are stored for each of the probes. These stored offsets are used for determining whether or not the probe holder 26 and the probe array 30 are aligned with the X axis. FIG. 8 illustrates this step. On the grid in FIG. 8 the X axis base line 154 is intersected by 12 lines extending in the Y direction. The twelve intersections are the twelve nominal probe tip positions. The offsets of each of probes numbered 112 are plotted on the grid. These are indicated by the circles in FIG. 8. A least squares fit line 156 is calculated for the offset points, and the slope, or skew, designated by angle 158 is determined and compared with a maximum tolerance angle close to zero degrees. If the skew of the probe carrier 26 is excessive, the angle 158 is larger than the minimum tolerance angle, and the controller 64 provides an error indication including the amount of skew to be corrected. The operator then corrects the skew condition by adjusting the mounting of the probe carrier 26, bringing the least square fit line into alignment with the X direction.

Figure 9:
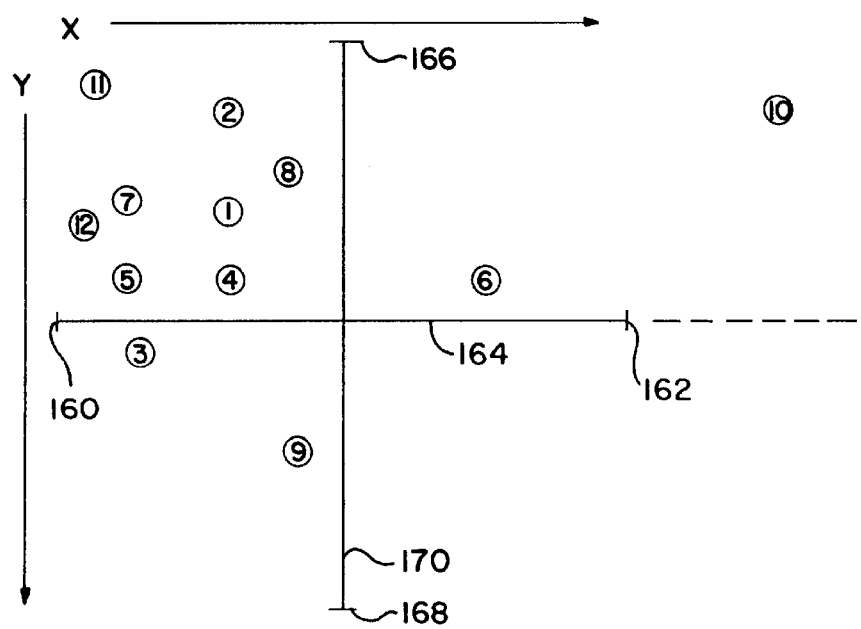
FIG. 9 is a scatter chart showing a probe tip cluster with one misaligned probe tip.

If probe carrier deskewing is needed, then after the skew condition is corrected, the probe tip position and offset measuring routine of FIGS. 5–7 is repeated for all probe tips, and the skew is checked again. If the skew angle 158 is now smaller than the minimum tolerance angle, then the method of the present invention proceeds with the correction of X-Y group scatter error. The probe tip position offsets as stored in block 150 (FIG. 6) for the twelve probe tips 36 are numbered 1–12 and are seen in the form of a scatter chart in the example of FIG. 9. A maximum range of X offset is indicated by the points 160 and 162 on the nominal or ideal X position line 164, and a maximum range of Y offset is indicated by the points 166 and 168 on the nominal or ideal Y position line 170. As seen in the example of FIG. 9, the offsets for probes 1–9, 11 and 12 are within the maximum X and Y bounds, However, the offset for probe 10 is beyond the maximum offset boundary in the positive X direction. This offset is unacceptable because it makes it impossible for the probe carrier 26 to reliably align all twelve probe tips 36 of the probe array 30 with targeted sample wells 66, In accordance with the present invention, the probe drive system 24 is used by the controller 64 to correct this measured probe tip misalignment. The drive system 24 again inserts the misaligned probe tip 36 into the locator well 76, and then moves the probe tip in the direction of the detected excessive offset. In the example of FIG. 9, the probe tip numbered 10 is inserted into the locator well 76 and moved in the positive X direction against the wall 88. The movement is large enough to exceed the limit of elastic deformation of the probe 34, and the probe 34 is deformed and bent so that the probe tip 36 is moved in the negative X direction relative to the other probe tips of the probe array 30. After his bending motion, the probe tip position and offset measurement routine of FIGS. 5–7 is repeated for the realigned probe tip 36, and, if necessary, the probe deformation process is repeated until the misaligned probe tip is within the boundaries of maximum offset. This corrected position of probe numbered 10 can be seen in FIG. 10.

Figure 10:
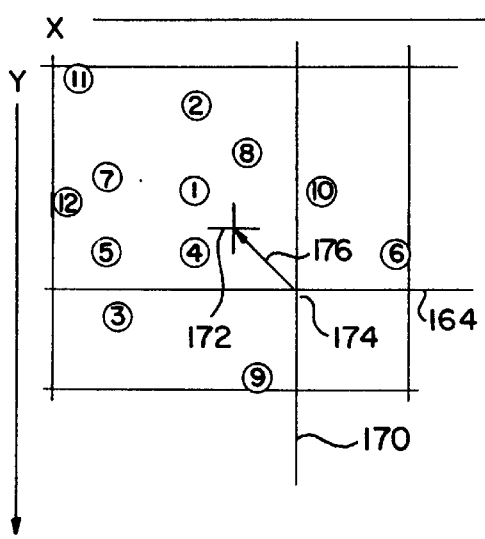
FIG. 10 is a view like FIG. 9 showing correction of the probe tip misalignment, and showing the offset of the cluster center from the nominal center.
Figure 11:
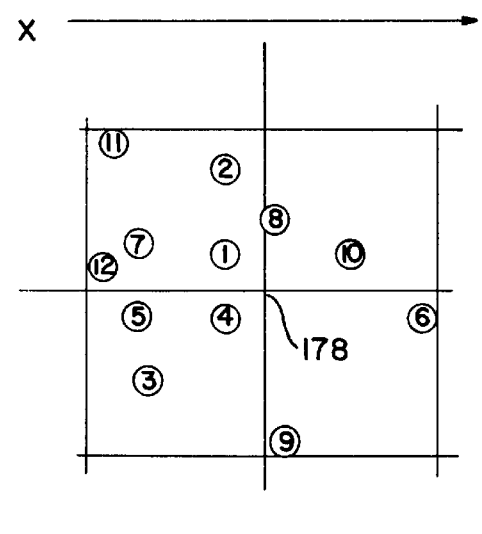
FIG. 11 is a view like FIG. 10 showing correction for the cluster center offset using a global correction factor.

When all the twelve probes are in an acceptable, tight cluster inside the maximum offset ranges 160, 162, 166 and 168 of the scatter chart (FIG. 9), then a global correction factor is calculated for use by the controller 64 in operating the probe drive system 24. FIG. 10 shows the twelve offset points before correction. The maximum and the minimum X offsets (probes 6 and 12) are averaged, and the maximum and minimum Y offsets (probes 9 and 11) are averaged to provide X and Y offset coordinates for the center of the scattered cluster group. In the example of FIG. 10, the center is at point 172, and this center is offset from the nominal or ideal center 174 by offset line 176. Rather than attempting to physically move or reposition the probe tips 36 to center the clustered probe array 30, the offset 176 is stored by the controller 64 as a global correction factor. When the controller 64 moves the probe holder 24 to a desired position over the locator bed 28, the target X and Y coordinates are modified by the global correction factor 176. As a result the scattered cluster is effectively repositioned to a corrected position indicated graphically in FIG. 11 where the nominal center 174 and the cluster center 172 of FIG. 10 are seen to coincide at the point 178.

The stored probe tip offset information is also used to check the alignment of the locator bed 28 on the work bed 22 of the liquid handler 20. The left most probe tip 36 (FIG. 4) is inserted into the locator well 80, and the position measuring routine of FIGS. 5–7 is carried out to obtain offset coordinates for the left probe in the locator well 80. The right most probe tip 36 (FIG. 4) is inserted into the locator well 78, and the position measuring routine of FIGS. 5–7 is again carried out to obtain offset coordinates for the right probe in the locator well 78. Because the actual positions of the left and right probes are known relative to the central locator well 76, the Y offset coordinates of the probe tips 36 in the laterally spaced locator wells 78 and 80 are compared with the Y offset coordinates of the same probe tips 36 in the well 76. If a discrepancy is detected, a determination is made that the locator bed 28 is skewed upon the work bed 22. The controller 64 provides an error message including the information needed for the operator to readjust the position of the locator bed 28 and correct the locator bed skew condition.

While the present invention has been described with reference to the details of the embodiment of the invention shown in the drawing, these details are not intended to limit the scope of the invention as claimed in the appended claims.

What is claimed is:

1. A probe tip alignment method for a precision liquid handler having a probe array moved by a probe drive system relative to a locator bed holding sample wells, said method comprising performing the following steps:

sequentially inserting the probe tips of the probe array with the probe drive system into a locator well at a known position on the locator bed; and sequentially sensing the position of each probe tip in the locator well; and mapping the positions of the probe tips.

2. A probe tip alignment method as claimed in claim 1, said sensing including moving the probe tip into contact with spaced points on a side wall of the locator well, and detecting contact between the probe tip and the side wall.

3. A probe tip alignment method as claimed in claim 1, further comprising overlaying the mapped positions of the probe tips to derive probe tip scatter.

4. A probe tip alignment method as claimed in claim 3, further comprising finding a center of the probe tip scatter and storing the center as a global correction factor for the probe drive system.

5. A probe tip alignment method as claimed in claim 3, further comprising screening the probe tip positions to identify any excessively misaligned probe tip;

using the probe drive system to place any identified probe tip into contact with a rigid part of the locator bed; and driving the identified probe against the rigid part to bend the identified probe into an aligned position.

6. A probe tip alignment method as claimed in claim 5 wherein the rigid part employed in the using and driving steps is the locator well.

7. A probe tip alignment method as claimed in claim 1, further comprising checking the mapped positions of the probe tips for skew of the probe array.

8. A probe tip alignment method as claimed in claim 1, further comprising:

using probe tips with mapped positions to locate two spaced apart locator points on the locator bed and comparing the two spaced apart locator points with the mapped positions in order to detect skew of the locator bed.

* * * * *